United States Patent [19]
Jeng

[11] Patent Number: 5,865,828
[45] Date of Patent: Feb. 2, 1999

[54] COAXIAL DUAL LASER

[76] Inventor: James C. Jeng, 7303 Broxburn Ct., Bethesda, Md. 20817

[21] Appl. No.: 907,622

[22] Filed: Aug. 8, 1997

[51] Int. Cl.[6] ................................................. A61B 17/36
[52] U.S. Cl. ...................................... 606/2; 606/9; 606/11
[58] Field of Search .................................. 606/2, 3, 9–11, 606/13, 17, 18

[56] References Cited

U.S. PATENT DOCUMENTS

| | | | |
|---|---|---|---|
| 4,576,177 | 3/1986 | Webster, Jr. | 606/17 |
| 4,887,605 | 12/1989 | Angelsen et al. | 606/18 |
| 5,029,588 | 7/1991 | Yock et al. | 606/18 |
| 5,217,456 | 6/1993 | Narciso, Jr. | 606/16 |
| 5,275,594 | 1/1994 | Baker et al. | 606/15 |
| 5,293,872 | 3/1994 | Alfano et al. | 606/14 |
| 5,496,305 | 3/1996 | Kittrel et al. | 606/15 |

*Primary Examiner*—Lee Cohen
*Assistant Examiner*—Bryan K. Yarnell
*Attorney, Agent, or Firm*—Akin, Gump, Strauss, Hauer & Feld, LLP

[57] ABSTRACT

A process and apparatus for ablating surface lesions is disclosed. The process is unique because of the ability to precisely excise complex topographies without blood loss, gated by the degree of surface small vessel blood flow via detection of Doppler shift. The most fitting application is the immediate, bloodless, and precise excision of thermal burn wounds, hitherto impossible and extremely desirable. A variation of the invention is disclosed which incorporates gating both by surface small vessel blood flow and fluorescence tagging. This embodiment has particular application in ablating neoplasms.

20 Claims, 6 Drawing Sheets

Laser Doppler detection of cutaneous blood flow, details

Figure 4
Gating areas to ablate, details

Figure 5
Ablating tissue, details

Figure 6
Dual gating to fluorescence and blood flow

COAXIAL DUAL LASER

FIELD OF THE INVENTION

The present invention relates to a coaxial dual laser system, and in particular a coaxial dual laser system particularly useful for the ablation of undesired tissue, including burn tissue.

BACKGROUND OF THE INVENTION

The present invention addresses the pressing need to be capable of surgically excising surface lesions with a discrimination of tissue to be removed/tissue to remain at the millimeter level. Using the principal of Doppler shift, the process and apparatus disclosed discriminates desirable from undesirable tissue by the degree of small vessel blood flow at the surface, with a resolution limited only to the width of the scanning laser Doppler beam. This degree of surgical resolution or precision has never been remotely approached by a surgeon wielding a scalpel.

Incumbent upon any "tangential excision" of surface lesions is the ability to remove the lesion without hemorrhaging the patient to death, a real world concern and rate limiting step with this type of surgery. The process and apparatus disclosed works bloodlessly by virtue of the cauterizing effects of the ablating laser beam. Bloodless tangential excision would allow the scope of an excision not to be limited by blood loss, but by the endurance of the operative team. The present inventor is unaware of such bloodless tangential excision having been realized heretofore.

A very fitting application for the disclosed process and apparatus is the immediate (vs. early) excision and grafting of major burn injuries. Again, the present inventor is unaware of such immediate excision having been realized heretofore. Major burns remain one of the most devastating traumatic injuries, with an annual mortality of >5000 people in the United States (1993), and 80,000 hospitalizations per year. The suffering is especially severe in the pediatric population, where the burns are frequently a result of child abuse.

Early excision and grafting of burns (within five days of injury) has been the principal engine behind improvements in burn mortality over the last twenty years (Effects of early tangential excision and grafting on survival after burn injury. Cryer HG, Anigian GM, Miller FB, et al. Surg Gynecol Obstet 1991 Dec;173(6):449–53). Because of the intensity of the physiologic derangements resulting from burns, the period of resuscitation from burn shock has essentially precluded operative excision of the burns, with its attendant massive blood loss (Burn shock resuscitation. Warden GD. World J Surg 1992 Jan–Feb:16(1):16–23).

The burn wound represents a site of life threatening bacterial infection as well as a lost barrier to microorganism infiltration. Immediate excision and closure of burn wounds remains an important goal of current research to improve outcomes (Early, complete burn wound excision partially restores cytotoxic T lymphocyte function. Hultman CS, Cairns BA, deSerres S, et al. Surgery 1995 Aug;118(2):421–9). If immediate and complete excision of clinical burns were possible, it would represent a quantum leap in the standard of care and be the basis for a dramatic increase in survivorship. The present invention permits this very goal to be achieved.

Other significant clinical problems that would be well addressed by the invention include, but are not limited to, management of decubitus ulcers (bed sores), all non-healing ulcers of the skin, and the precise, rapid debridement of necrotizing fasciitis and other mixed synergistic gangrenes. The latter two entities are dreaded aggressive soft tissue infections with high mortalities and limb loss.

Modified with an additional laser "channel" to excite, then quantify fluorescence from fluorescein or rhodamine tagged monoclonal antibodies, the invention becomes useful in the ablation of tumors. Conceptually, this scheme capitalizes on the fact that nearly all cancerous tumors are hyper-vascular relative to normal tissues, a condition that can be identified by Doppler shift (Role of color Doppler imaging in differentiating between pseudocystic malignant tumors and fluid collections. Fornage BD, J Ultrasound Med 1995 Feb:14(2):125–8). The duality of gating control would allow for discrimination of nonspecific fluorescein or antibody binding by "double checking" with blood flow parameters.

Several prior patents exist that describe the use of lasers for the ablation of tissue. None of them disclose or suggest a combination which includes Doppler shift analysis of tissue blood-flow to control or "gate" the ablating laser.

There are five U.S. Pat. Nos. 5,558,432 (Crowley), 5,010,886 (Passafaro et al.), 4,887,605 (Angelsen et al.), 4,785,806 (Deckelbaum), 4,587,972 (Morantte Jr.) that deal with delivery of wave energy (typically a laser) via a flexible catheter into the intra-vascular space to diagnose and/or ablate a cardiovascular lesion. These lesions are either atheromas causing intralumenal obstruction (blockage of arteries), or foci of aberrant electrical activity in the heart (irregular heart beat). The field of these five patents is cardiovascular, intralumenal medicine.

In U.S. Pat. No. 5,608,520 (Fleming), a method of tumor ablation is described using a laser to vaporize target tissue with the resultant spectral analysis of light emitted employed in gating further ablation. Although comment is made to application in Doppler interferometry, Doppler analysis of blood flow and derivative control and gating of the ablating laser is not described, nor a logical derivative of the information and design disclosed.

In U.S. Pat. No. 4,973,848 (Kolobanov et al.), an "analysis beam" is used to excite a fluorescent dye tagged target which then derives control and gating of a "treatment beam". In the preferred embodiment, these two lasers are convergent, and not coaxial (although feasibility of a coaxial light path is remarked upon). The stated fields include industrial materials processing, dermatology, cosmetic surgery, and tumor therapy. No incorporation of Doppler analysis of blood flow in the "analysis beam" appears to be mentioned. Using blood flow as the means of controlling the treatment beam would not be a logical derivative of the design as disclosed.

In U.S. Pat. No. 4,932,412 (Goldenberg), a process of endoscopic or intra-cavitary ablation of tumor is described which depends on recognition of tumor tissue with radio-immunodetection. This analysis is then potentially used to control and gate an ablative laser. The stated field here is gastrointestinal malignancies.

In U.S. Pat. No. 4,672,963 (Barken), a process and apparatus is described in which target tissue is analyzed with two-dimensional ultrasound. Visual control and gating from the ultrasound image then drives ablation with a laser. The preferred embodiment was demonstrated managing a tumor of the prostate gland.

The preceding four US patents all deal with the destruction of tumors or other undesirable tissue with lasers. One aspect which clearly separates these examples of prior art from the present invention is the analysis of tissue blood flow by Doppler shift to control and gate the ablative laser.

Furthermore, in none of these four patents are two lasers combined optically coaxial. The coaxial nature of the present invention is a significant (but not mandatory) design feature of the present invention, in its preferred embodiment.

Furthermore, in none of these four patents is the optical axis manipulated by a precisely controlled mirror, which streamlines the form factor of a physical embodiment of the design, and provides a high gain in collecting returned wave energy.

Lastly, in none of these four patents is the process and apparatus specifically nor easily adaptable to the rapid excision of clinical burns or soft tissue infections in a bloodless fashion, an important design feature of the present invention, in its preferred embodiment. Although use in tumor therapy was described in the prior art, no addressing of that therapy in a bloodless, cauterizing fashion appears to be disclosed.

It is therefore an object of the present invention to provide for a means to tangentially excise burn wounds immediately upon arrival in the intensive care unit, even in the midst of resuscitation from burn shock.

It is further an object of the present invention to provide for a resolution of normal vs. abnormal tissue (burns or otherwise) at the millimeter level, a precision not previously attainable by any method.

It is further an object of the present invention to provide control for a coaxial ablative laser by gating to surface small vessel blood flow determined by Doppler shift.

It is further an object of the present invention to tangentially excise a burn wound or other tissue lesion bloodlessly by using an ablative laser which cauterizes as well.

It is further an object of the present invention to incorporate selectable wavelengths of the Doppler laser so that the depth of blood flow analysis is variable.

It is further an object of the present invention to incorporate selectable beam width, laser power, dwell time adjustment, and scanning raster adjustment for the ablative laser so that the ablation can be fine-tuned to minimize collateral thermal tissue damage.

It is further an object of the present invention to employ control logic so that a re-analysis of blood flow is done after each ablative cycle (nominally 200 $\mu$m ablation depth per cycle) to maximize the depth precision of tissue excision.

It is further an object of the present invention to allow for high-pass or low-pass blood flow gating of ablation so that the device may be used to ablate tumors or soft tissue infections characterized by a higher than normal blood flow.

It is further an object of the present invention to allow for insertion of a second diagnostic laser channel set up to excite and detect fluorescence from dye tagged monoclonal antibodies adherent to target tissues. In this mode, gating of the ablative laser would be dual: to blood flow and to presence of fluorescent tagged antibody binding.

It is further an object of the present invention to incorporate adjustments to the ablating laser such that dwell time can be modified by motion dither introduced by ultrasonic vibration of elements in the optical path.

It is further an object of the present invention to employ a control electronics suite and logic sufficient to permit treatment of the whole surface area of an adult in the span of several hours.

It is further an object of the present invention to incorporate digital image stabilization to overcome un-preventable patient motion.

SUMMARY OF THE INVENTION

In accordance with the present invention, in its preferred embodiment, these and other objectives are achieved by providing a device for ablating tissue, comprising a first laser channel and a second laser channel. The first laser channel and the second laser channel are coaxial. The first laser channel is controlled to detect blood flow in a target via Doppler shift analysis. Means are provided for identifying desired tissue and undesired tissue in the target in accordance with the blood flow detected via Doppler shift analysis. The second laser channel is controlled in response to the Doppler shift analysis to ablate the undesired tissue. Topographically complex tissue is thereby precisely excised from the target with minimal blood loss, leaving a sterile surface free of undesired tissue.

BRIEF DESCRIPTION OF THE DRAWINGS

A detailed description of a preferred embodiment of the present invention will be made with reference to the accompanying drawings.

DETAILED DESCRIPTION OF THE PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is best defined by the appended claims.

In the illustrated preferred embodiment the coaxial dual laser may be used for burn ablation. However, the present invention is not limited to the treatment of burns. The scope of clinical problems amenable to the process and apparatus include lesions on any surface that can be reached by the optical axis, selected by quantifying surface blood flow, ± presence of fluorescence-tagged monoclonal antibodies. These and other applications will be apparent to one skilled in the art.

Burn victims are moved from the field to the receiving area of the burn facility by prehospital emergency medical services. After determining the presence of partial or full thickness burns by the clinician, the patient is admitted to the intensive care unit where the patient is typically intubated, ventilated, and sedation, analgesia, and paralysis are established. Fluid resuscitation for burn shock proceeds in the normal fashion, with administration of fluid resuscitation to the traditional endpoint of adequate urine output. Pressor drugs (those that cause constriction of blood vessels) are avoided during the treatment period. Hypothermia (low body temperature) is corrected prior to initiation of the process so that absence of blood flow due to shunting away from the skin envelope does not skew the operation of the device and protocol.

The area of the burn wound is exposed. Povidone iodine (Betadine) skin preparation (to sterilize the surface) is followed by cleansing the site with sterile normal saline. A sterile surgical drape may then be placed around the field in accordance with usual operating room aseptic technique. The instrument may then be draped with a sterile plastic sleeve, and then brought onto the field.

Figure 1:
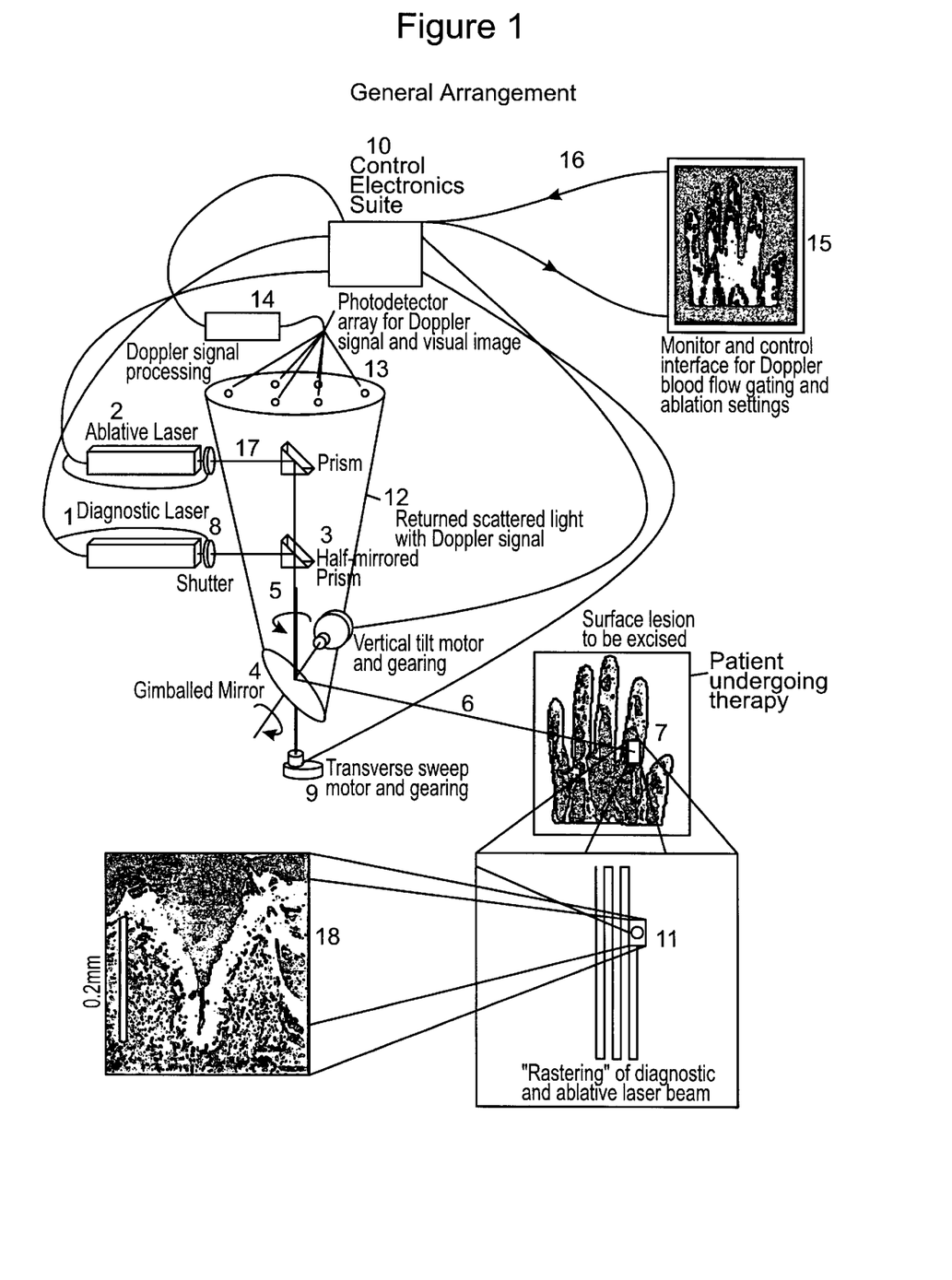
FIG. 1 illustrates an example of a general overall arrangement of one embodiment of a process and apparatus for ablating tissue.

Referring in particular to FIG. 1, in the illustrated preferred embodiment the present invention comprises a laser Doppler light source (1) and an ablative $CO_2$ laser (2) with a variable output up to 150 W. The laser Doppler light source (1) may include, for example, those made by LISCA Corp. or Moor Instruments. The ablative $CO_2$ laser (2) may include, for example, the Diamond 64 Laser made by the Coherent Laser Group, Palo Alto, Calif. The two lasers are made coaxial via prisms, one of which may be half mirrored (3) to admit passage of both beams towards a gimbaled mirror (4) which then directs the optical axis (5,6) onto the target tissue (7). Alternating the lasers may be managed by shutters (8) of either a mechanical or power interrupting mechanism. The mirror may be precisely swept through vertical and horizontal axes by precision DC motors and reduction gear assemblies (9) governed by the control electronics suite incorporating digital image stabilization (commonly found in video camcorders made by Sony and Canon) (10). See below for a description of one example of the logic algorithm. The mirror control logic directs a scanning motion of the optical axis in a raster upon the target tissue (11). Scattered laser light from the diagnostic beam containing Doppler shift information (12) may be collimated by the mirror and returned to a multiple assembly of photo-detectors (examples, LISCA Corp. or Moor Instruments, 13), which then undergo processing to extract blood flow data from the Doppler shift (14). An image with false coloring keyed to Doppler blood flow at the tissue surface may then be displayed on a monitor/control interface counsel (15). User selectable gating to Doppler flows may then be relayed to the control electronics (16) which then fires the ablating laser beam at targets within the gated blood f low parameters (17), vaporizing 200 $\mu$m of tissue at a time (18), cauterizing as it ablates. The control electronics suite (10) will incorporate pattern recognition capabilities for (example) tendons, blood vessels, and other as yet to be defined anatomical structures. These structures may require special gating considerations due to their geometry or characteristic low/high blood flow that may not fit neatly within the standard control logic described below.

Figure 2:
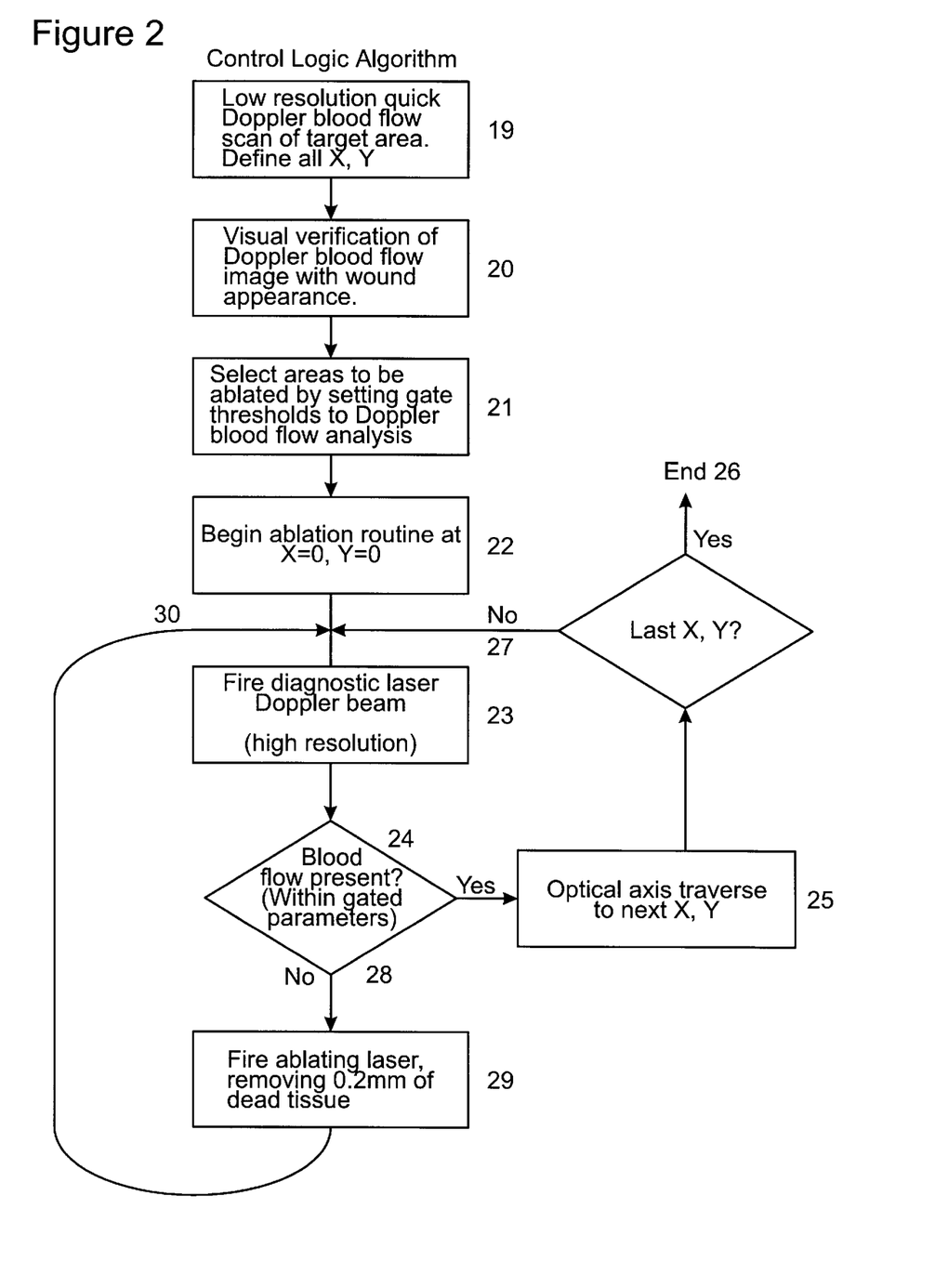
FIG. 2 illustrates an example of a flow diagram of a control logic algorithm for the disclosed process and apparatus.

Referring to FIG. 2, in the preferred embodiment the control electronics suite may be built to the following logic: An initial rapid, low resolution (spatially) Doppler blood flow scan may be made of the target tissue and displayed on the monitor. From this image, the treatment area, all X and all Y, may be selected (19). The clinician-operator then verifies that the acquired and selected target matches a visual examination of the target tissue (20). By examining the false color rendition quantifying blood flow at the surface level, the path of the ablating laser may be gated to a clinician defined degree of blood flow (21). These levels will correspond clinically to (for example) $2^{nd}$ and $3^{rd}$ degree burns, areas of skin and soft tissue necrosis from ischemia, pressure, infection, or neoplastic (cancerous) change. Once the gating is defined, the apparatus then shifts into the active ablation routine starting with the first X, Y coordinate (22). The Doppler laser may be again fired, now in a high resolution mode (spatially), at the first coordinate (23). The resolution and depth of blood flow analysis may be clinician definable by control of the beam width and selection of the laser frequency employed for Doppler analysis. At this point the Doppler "query" returns with a yes/no answer to the question: Blood flow present at X, Y within the gated parameters (24)? If the reply is yes (tissue is alive/desirable), the logic directs rastering to the next coordinate (25). If the next coordinate is the last X, Y, the ablation is complete and ends (26). If not, the "presence of blood flow" query cycle begins again (27).

If blood flow is not detected (28), a permissive signal may be sent to fire the ablating laser, which then vaporizes 200 $\mu$m of tissue (29). The diameter of the ablation will be determined by pulse time, beam width, power output, and motion "dither" to introduce variable dwell time at any particular pinpoint within the area being ablated (see FIG. 5, ablation). After vaporizing 200 $\mu$m of tissue, the diagnostic Doppler laser may be again brought on line to reassess for the presence of blood flow (tissue is alive) (30). In this way, at each X, Y coordinate, ablation of dead tissue proceeds in 200 $\mu$m increments until all dead tissue may be removed and a base of living tissue may be exposed. The ablation may be bloodless by virtue of the cauterizing nature of the $CO_2$ laser employed.

Figure 3:
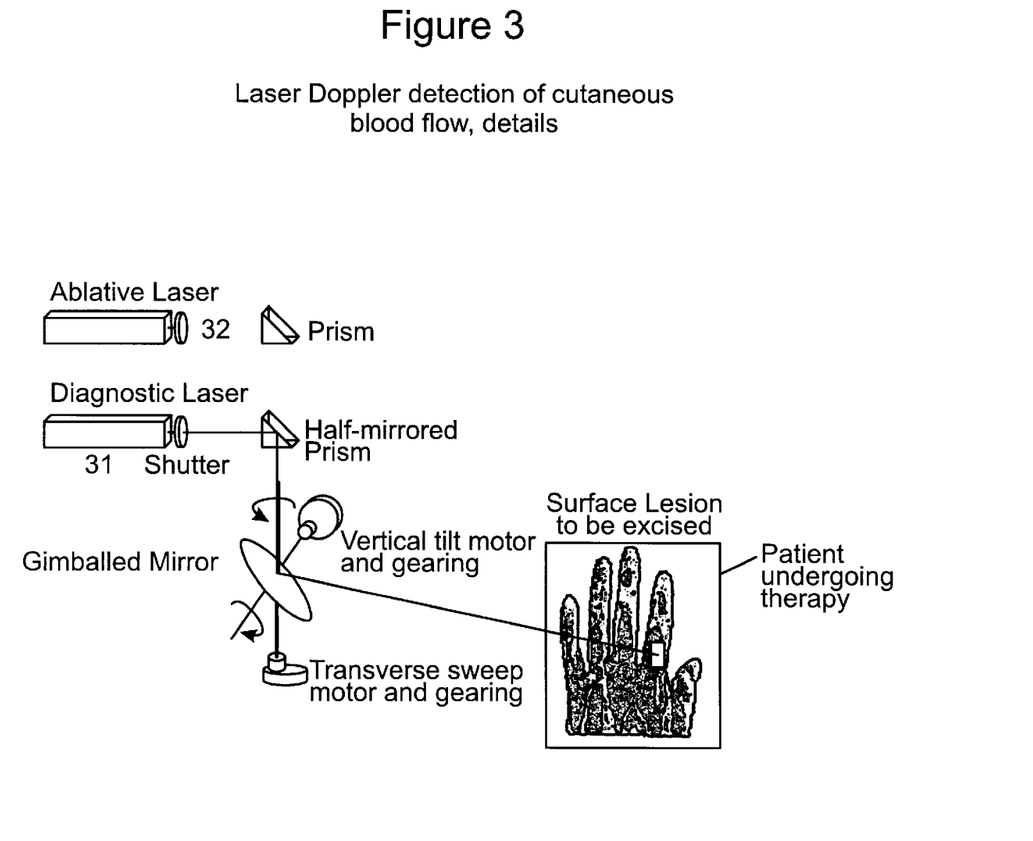
FIG. 3 illustrates an example of a schematic diagram of an apparatus as it queries a target coordinate for the presence or absence of blood flow by Doppler shift.

Referring to FIG. 3, as described in the control logic algorithm above, in the preferred embodiment the surface blood flow may be instantaneously determined by measuring the resulting Doppler shift of a low powered (example 1.5 mW, 1.0~5.0 mm beam width) red laser (633 nm wavelength) or near infra-red laser (780 or 810 nm wavelength), depending on the blood flow depth of interest (31). The ablative laser is off for this cycle of the operation (32). The scattered light may be collected by the mirror, and then returned to the photo-detectors, Doppler signal processing, and then to the control electronics suite as described above.

Figure 4:
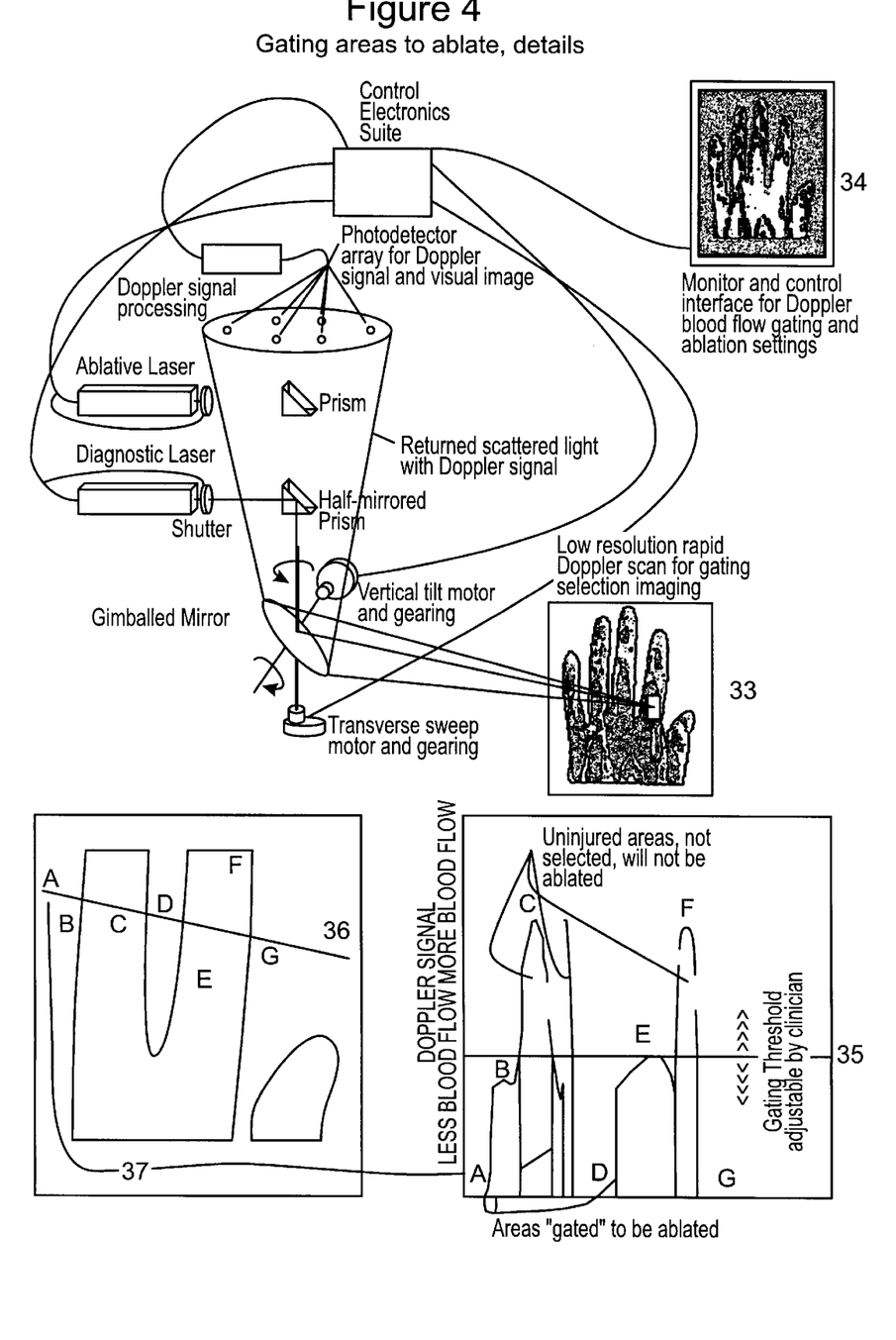
FIG. 4 illustrates an example of a schematic diagram of a process of gating an ablative laser to laser Doppler blood flow analysis.

Referring to FIG. 4, as described above, in the preferred embodiment the process begins with a quick low resolution Doppler scan for gating purposes (33). After processing and displaying the Doppler shift information, the clinician reviews the default visual description of what tissue is alive (has blood flow, do not ablate) and dead (has no blood flow, tag for ablation) presented in false colors (34). This default setting can be fine tuned by setting the Doppler signal threshold at which to tag tissue as alive or dead (35). Information can be displayed in a linear fashion, which also clarifies the gating selection process (36). The letters in both diagrams correlate to each other (37).

Figure 5:
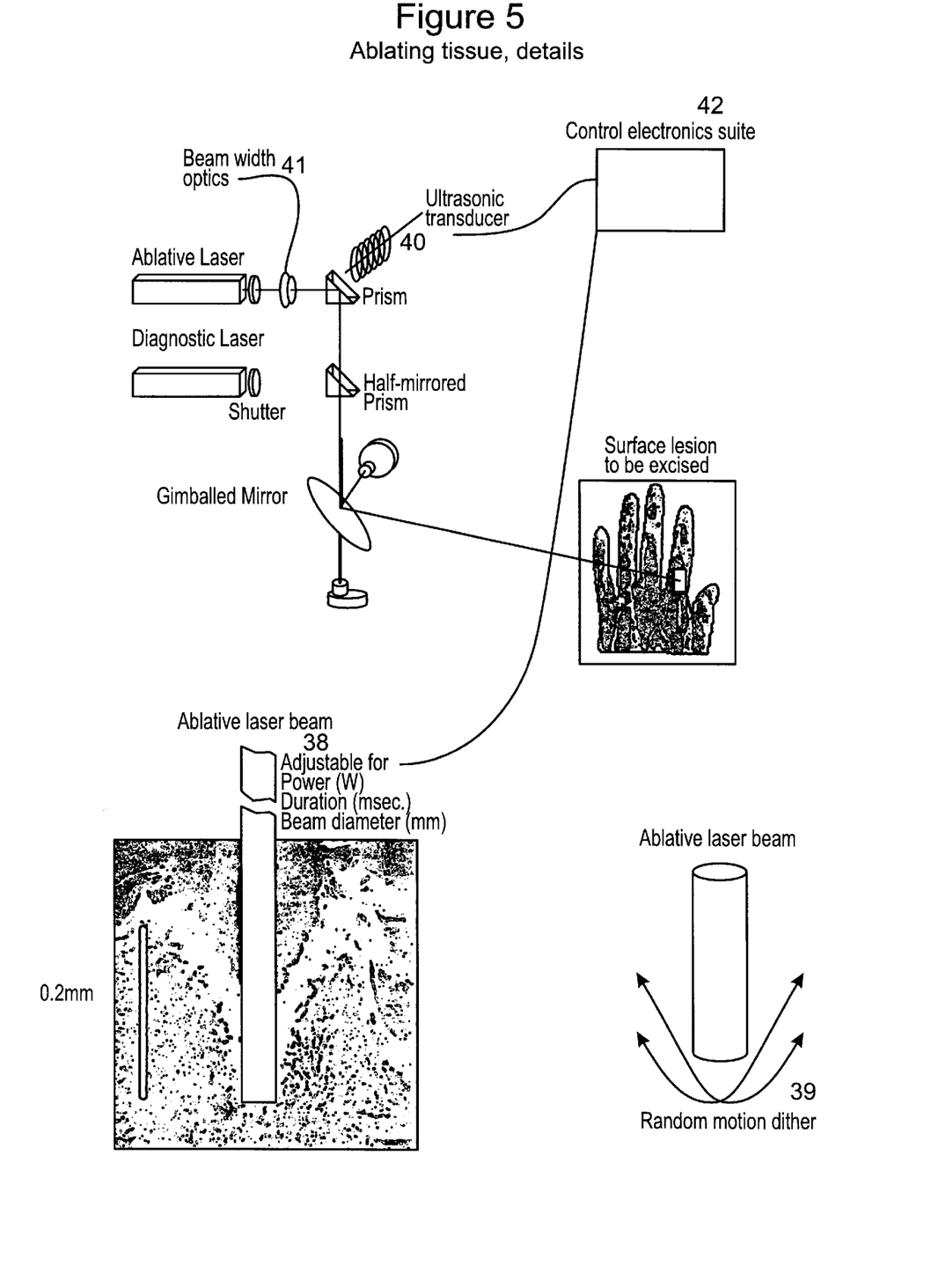
FIG. 5 illustrates an example of a schematic diagram of an ablative phase of the cycle.

Referring to FIG. 5, during the ablation phase of operation in the preferred embodiment, the diagnostic Doppler laser is shut off, and the CO2 laser fires a burst which may be controllable for power, duration, diameter of beam (38) and dwell time by virtue of motion dithering in the plane of ablation (39). This dither, or random motion may be introduced by an ultrasonic transducer attached to an optical element in the light path of the ablating beam, for example, the prism (40). The transducer may be of the type used in ultrasonic liquid immersion cleaners, with adjustable volume to adjust the amplitude of the random motion. Beam width may be adjusted optically (41). Power output and duration may be adjusted by means of the control electronics suite (42).

Figure 6:
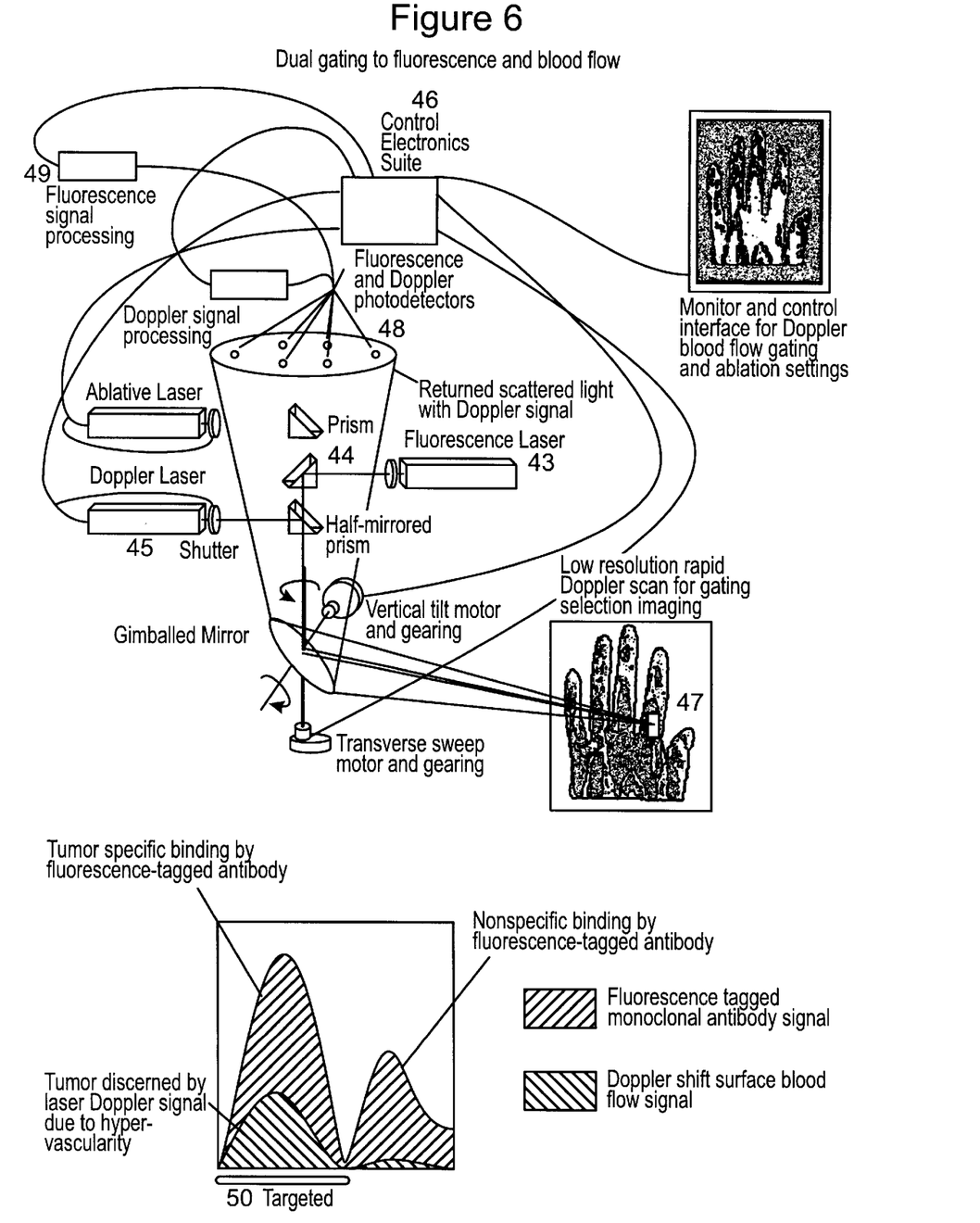
FIG. 6 illustrates an example of a schematic diagram of an apparatus set up to gate to both blood flow and binding of fluorescent tagged antibodies.

Referring to FIG. 6, in one preferred embodiment the instrument can be arranged with an additional gating channel, activated by a separate diagnostic laser with wavelength appropriate to the fluorescent dye employed (43), coaxial via yet another half-mirrored prism (44). Diagnostics on the target tissue is now gated both to blood flow by Doppler laser (45), and fluorescence (43), with the two lasers being fired alternately by the control electronics suite (46). The target tissue may be stained with fluorescent dye tagged monoclonal antibodies to (examples) a tumor surface marker (ablation of a surface tumor) or a bacterial antigen (ablation of infected tissues in soft tissue infections) which then fluoresces at a defined wavelength when illuminated by the laser light (47). Returned fluorescent light may then be measured by the photo-detector array (48), and the signal processed for the specific frequency (49), and then passed to the control electronics suite (46) for gating selection. Gating of ablation can be done now so that only coordinates which fall within gating to both fluorescent tagging and cutaneous blood flow are targeted for the $CO_2$ laser (50).

The presently disclosed embodiments are to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for ablating tissue, comprising:
   providing a first laser channel,
   providing a second laser channel, the first laser channel and the second laser channel being coaxial,
   controlling the first laser channel to detect blood flow in a target via Doppler shift analysis,
   identifying at least one of desired tissue and undesired tissue in the target in accordance with the blood flow detected via Doppler shift analysis,
   controlling the second laser channel in response to the Doppler shift analysis to ablate the undesired tissue,
   whereby topographically complex tissue is precisely excised from the target with minimal blood loss, leaving a sterile surface free of undesired tissue.

2. The method of claim 1, comprising:
   tagging monoclonal antibodies in the target with at least one of a fluoresceine or rhodamine dye,
   providing a third laser channel for exciting the dye tagged monoclonal antibodies,
   controlling the third laser channel to detect fluorescence from the dye tagged monoclonal antibodies,
   controlling the second laser channel in response to the Doppler shift analysis
   and to the detected fluorescence from the dye tagged monoclonal antibodies to ablate the undesired tissue.

3. The method of claim 1, wherein the undesired tissue comprises hyper-vascular tissue.

4. The method of claim 1, wherein the undesired tissue defines a depth, wherein the second laser channel originates from a laser source, wherein the laser source has a pulse duration and a wattage, and comprising the step of:
   modifying at least one of the pulse duration and the wattage of the laser source to thereby modify the depth of undesired tissue ablated by the second laser channel.

5. The method of claim 1, wherein the first laser channel and the second laser channel define an optical axis, and comprising:
   moving the optical axis from a first location in the target to a second location in the target after the step of controlling the second laser channel to ablate undesired tissue,
   repeating, at the second location, the steps of controlling the first laser channel to detect blood flow via Doppler shift analysis, identifying at least one of desired tissue and undesired tissue, and controlling the second laser channel in response to the Doppler shift analysis to ablate the undesired tissue.

6. The method of claim 1, wherein the target defines a plurality of locations and wherein, at each of the plurality of locations, the steps of controlling the first laser channel to detect blood flow via Doppler shift analysis, identifying at least one of desired tissue and undesired tissue, and controlling the second laser channel in response to the Doppler shift analysis to ablate undesired tissue are repeated until desired tissue is detected.

7. The method of claim 5 or 6, comprising:
   selecting a blood flow threshold value which distinguishes undesired tissue and desired tissue, wherein the step of selecting a blood flow threshold value is performed after each ablation of undesired tissue.

8. The method of claim 1, comprising:
   generating an image of the target in which areas of desired tissue and undesired tissue are visually distinguishable.

9. The method of claim 1, comprising:
   selecting a blood flow threshold value which distinguishes undesired tissue and desired tissue.

10. The method of claim 1, wherein the second laser channel originates from a laser source defines a channel width, wherein the laser source has a laser power, a dwell time adjustment, and a scanning raster adjustment, and wherein the step of controlling the second laser channel comprises at least one of controlling the channel width, the laser power, the dwell time adjustment, and the scanning raster adjustment.

11. A device for ablating tissue, comprising:
   a first laser channel,
   a second laser channel, the first laser channel and the second laser channel being coaxial,
   means for controlling the first laser channel to detect blood flow in a target via Doppler shift analysis,
   means for identifying at least one of desired tissue and undesired tissue in the target in accordance with the blood flow detected via Doppler shift analysis,
   means for controlling the second laser channel in response to the Doppler shift analysis to ablate the undesired tissue,
   whereby topographically complex tissue is precisely excised from the target with minimal blood loss, leaving a sterile surface free of undesired tissue.

12. The device of claim 11, wherein monoclonal antibodies in the target are tagged with at least one of a fluoresceine or rhodamine dye, comprising:
   a third laser channel for exciting the dye tagged monoclonal antibodies,
   means for controlling the third laser channel to detect fluorescence from the dye tagged monoclonal antibodies, and
   means for controlling the second laser channel in response to the Doppler shift analysis and to the detected fluorescence from the dye tagged monoclonal antibodies to ablate the undesired tissue.

13. The device of claim 11, wherein the undesired tissue comprises hyper-vascular tissue.

14. The device of claim 11, wherein the undesired tissue defines a depth, wherein the second laser channel originates from a laser source, wherein the laser source has a pulse duration and a wattage, and comprising:

means for modifying at least one of the pulse duration and the wattage of the laser source to thereby modify the depth of undesired tissue ablated by the second laser channel.

15. The device of claim 11, wherein the first laser channel and the second laser channel define an optical axis, and comprising:

means for moving the optical axis from a first location in the target to a second location in the target after the step of controlling the second laser channel to ablate undesired tissue, means for repeating, at the second location, the steps of controlling the first laser channel to detect blood flow via Doppler shift analysis, identifying at least one of desired tissue and undesired tissue, and controlling the second laser channel in response to the Doppler shift analysis to ablate the undesired tissue.

16. The device of claim 11, wherein the target defines a plurality of locations and comprising means for repeating, at each of the plurality of locations, the means for controlling the first laser channel to detect blood flow via Doppler shift analysis, identifying at least one of desired tissue and undesired tissue, and controlling the second laser channel in response to the Doppler shift analysis to ablate undesired tissue until desired tissue is detected.

17. The device of claim 15 or 16, comprising:

means for selecting a blood flow threshold value which distinguishes undesired tissue and desired tissue, wherein the means for selecting a blood flow threshold value is performed after each ablation of undesired tissue.

18. The device of claim 11, comprising:

means for generating an image of the target in which areas of desired tissue and undesired tissue are visually distinguishable.

19. The device of claim 11, comprising:

means for selecting a blood flow threshold value which distinguishes undesired tissue and desired tissue.

20. The device of claim 11, wherein the second laser channel originates from a laser source defines a channel width, wherein the laser source has a laser power, a dwell time adjustment, and a scanning raster adjustment, and wherein the means for controlling the second laser channel comprises at least one of controlling the channel width, the laser power, the dwell time adjustment, and the scanning raster adjustment.

* * * * *